(12) United States Patent
Muscatelli et al.

(10) Patent No.: US 9,353,456 B2
(45) Date of Patent: May 31, 2016

(54) PROCESS FOR OBTAINING A CHARGE OF HEXANITROHEXAAZAISOWURTZITANE CRYSTALS HAVING A ROUNDED MORPHOLOGY; CHARGE AND CORRESPONDING ENERGETIC MATERIAL

(75) Inventors: Florent Muscatelli, La Ferte Alais (FR); Philippe Lescop, Vert le Petit (FR)

(73) Assignees: HERAKLES, Le Haillan (FR); EURENCO, Massy (FR)

( * ) Notice: Subject to any disclaimer, the term of this patent is extended or adjusted under 35 U.S.C. 154(b) by 105 days.

(21) Appl. No.: 14/110,621

(22) PCT Filed: Apr. 5, 2012

(86) PCT No.: PCT/FR2012/050733
§ 371 (c)(1),
(2), (4) Date: Nov. 26, 2013

(87) PCT Pub. No.: WO2012/136933
PCT Pub. Date: Oct. 11, 2012

(65) Prior Publication Data
US 2014/0073781 A1 Mar. 13, 2014

(30) Foreign Application Priority Data

Apr. 8, 2011 (FR) ..................................... 11 53065

(51) Int. Cl.
| C07D 487/22 | (2006.01) |
| C06B 25/34 | (2006.01) |
| C30B 7/06 | (2006.01) |
| C30B 29/54 | (2006.01) |

(52) U.S. Cl.
CPC . *C30B 7/06* (2013.01); *C06B 25/34* (2013.01); *C07D 487/22* (2013.01); *C30B 29/54* (2013.01)

(58) Field of Classification Search
CPC .............................. C07D 487/22; C06B 25/34
USPC ....................................................... 540/554
See application file for complete search history.

(56) References Cited

U.S. PATENT DOCUMENTS

| 5,973,149 A | 10/1999 | Bescond et al. |
| 7,789,980 B2 | 9/2010 | Benazet et al. |
| 2007/0225493 A1 | 9/2007 | Hamilton et al. |
| 2012/0199256 A1 | 8/2012 | Muscatelli et al. |

FOREIGN PATENT DOCUMENTS

| CN | 101624439 | 1/2010 |
| DE | 3605634 | 8/1987 |
| EP | 0913374 | 5/1999 |
| FR | 2858620 | 2/2005 |
| FR | 2884244 | 10/2006 |
| FR | 2887544 | 12/2006 |
| FR | 2950623 | 4/2011 |
| JP | 11-322752 | 11/1999 |

OTHER PUBLICATIONS

Japanese Office Action, Apr. 20, 2015; Japanese Patent Application No. 2014-503194 with English translaion (6 pages).
Eriksen; NATO Standardization Agency (NSA), Standardization Agreement (STANAG) STANAG 4488 (Edition 1)—Explosives, Shock Sensitivity Tests, Sep. 2002 (32 pages).
Mino R. Caira: "Crystalline Polymorphism of Organic Compounds"; Department of Chemistry, Topics in Current Chemistry, 1998, vol. 198, pp. 163-208.
Israeli Office Action (2 pages, with English summary), Jun. 29, 2015.

*Primary Examiner* — Brenda Colman
(74) *Attorney, Agent, or Firm* — Hamre, Schumann, Mueller & Larson, P.C.

(57) ABSTRACT

The present invention provides a process for obtaining a charge of hexanitrohexaazaisowurtzitane crystals having rounded morphology. It also provides said charge, the energetic material comprising it, and a process for manufacturing said material. Said process for obtaining said charge comprises:

preparing a saturated solution of any polymorphic form of hexanitrohexaazaisowurtzitane in a mixture comprising both an organic solvent for said hexanitrohexaazaisowurtzitane and an organic nonsolvent for said hexanitrohexaazaisowurtzitane, said solvent being more volatile than said nonsolvent;

seeding this saturated solution with a few hexanitrohexaazaisowurtzitane crystals; and then concentrating the seeded, saturated solution by at least partial evaporation of the solvent, said evaporation of the solvent being performed at a temperature of between 35° C. and 15° C. and at a pressure adjusted, to plus or minus 12 mbar, to the boiling pressure of the solvent in said solution, throughout the process of evaporating said solvent from said solution.

15 Claims, 2 Drawing Sheets

PROCESS FOR OBTAINING A CHARGE OF HEXANITROHEXAAZAISOWURTZITANE CRYSTALS HAVING A ROUNDED MORPHOLOGY; CHARGE AND CORRESPONDING ENERGETIC MATERIAL

The present invention relates to a process for obtaining a charge of hexanitrohexaazaisowurtzitane crystals, said crystals exhibiting a rounded morphology. The invention further pertains to said charge per se, to the energetic material comprising it, and to a process for manufacturing said material.

The invention is situated within the field of powders, propellants, and explosives, which are used in particular in the armament industries.

The crystals of the invention, which are obtained in the form of charges (untwinned crystals), have a rounded crystalline form which is particularly suitable for the formulation of energetic materials. This is set out in detail below.

For a number of years there have been numerous publications relating to 2,4,6,8,10,12-hexanitro-2,4,6,8,10,12-hexaazatetracyclo[5.5.0.0$^{5,9}$.0$^{3,11}$]dodecane, also called hexanitrohexaazaisowurtzitane or CL20. These publications describe the different polymorphic forms of this compound (it being known that hexanitrohexaazaisowurtzitane may be obtained in four polymorphic crystalline forms: beta, alpha, gamma, and epsilon); the physical, chemical, and detonating properties of this compound; and the use of said compound in explosive compositions, propellants, or powders for arms.

The epsilon polymorphic form of said compound (CL20ε) possesses the highest density (2.04 g/cm$^3$) and is therefore of the most interest, particularly for use in pyrotechnic compositions.

Patent application EP-A-0 913 374 describes a process for obtaining CL20ε according to the following reaction steps:
first of all a saturated solution of CL20 in any polymorphic form, preferably other than the epsilon form, is produced, in a mixture comprising both an organic solvent for the CL20, selected from the group consisting of esters, nitriles, ethers, ketones, with the exception of acetone, and mixtures thereof, and an organic nonsolvent for the CL20, selected from the group consisting of aliphatic hydrocarbons, aromatic hydrocarbons, and mixtures thereof, said solvent for the CL20 being more volatile than said nonsolvent (i.e., having a saturation vapor pressure lower than that of the nonsolvent) (said solvent and said nonsolvent being obviously miscible in the proportions used to constitute said mixture comprising CL20 (for obtaining a saturated solution of CL20));
this saturated solution is subsequently seeded with a few crystals of CL20ε; and then
said saturated, seeded solution is concentrated by evaporation of the solvent (causing the appearance of crystals of CL20ε in the nonsolvent-enriched mixture).

The saturated solution of CL20 may be prepared by two methods: preparation of a mixture of solvent+nonsolvent, then addition to said mixture of CL20 at saturation; or preparation of a mixture of nonsolvent+CL20 in excess, then addition to said mixture of the solvent, then filtration to remove the excess CL20.

The crystals or charge of crystals obtained may be recovered by any customary technique, such as filtration.

Examples of organic solvents for CL20 include methyl formate, methyl acetate, ethyl acetate, isopropyl acetate, acetonitrile, ethyl acetate/acetonitrile mixtures, tetrahydrofuran (THF), and methyl ethyl ketone. Acetone was excluded from the list of solvents that could be used because the performance of the process with that solvent (more specifically with the solvent/nonsolvent pairing of acetone/toluene) gave agglomerated crystals, the agglomerates or twins having a diameter of more than 100 μm (see example 4 of patent application EP-A-0 913 374).

Examples of organic nonsolvents for the CL20 include toluene, xylenes, alkanes such as hexane, heptane, and octane, and halogenated aliphatic hydrocarbons, especially chlorinated aliphatic hydrocarbons such as 1,2-dichloroethane.

Another class of organic nonsolvent for the CL20, the use of which in the above process (as per patent application EP-A-0 913 374) is described in patent application FR-A-2 950 623, consists of nonflammable hydrofluoroethers, such as 2-trifluoromethyl-3-ethoxy-1,1,1,2,3,4,4,5,5,6,6,6-dodecafluorohexane (referred to more simply hereinafter as 2-trifluoromethyl-3-ethoxydodecafluorohexane), of empirical formula $(CF_3)C_6F_{12}OC_2H_5$. This chemical compound bears the CAS number 297730-93-9. It is sold in particular by 3M under the trade name HFE 7500.

For performing the process above, particular preference is given to the following solvent/nonsolvent pairings: ethyl acetate/toluene, and ethyl acetate/HFE7500.

The solvent/nonsolvent ratio by mass is generally between 10/90 and 50/50, advantageously between 15/85 and 35/65.

During concentration of the solution (CL20-saturated solvent/nonsolvent mixture) by evaporation of the organic solvent, the temperature does not exceed 50° C. to 70° C., according to the nature of the solution in question, and that, in reference to the purity of the desired CL20 crystals.

In its example 5, patent application EP-A-0 913 374, for a solvent/nonsolvent pairing composed of ethyl acetate/toluene, describes evaporation of the solvent performed at ambient temperature (close to 20° C.) and at a low pressure of 6.25×10$^3$ Pa (62.5 mbar, approximately 50 mmHg). Such a pressure is very much lower than the boiling pressure of the solvent in the solution.

On the industrial scale, preference is given to working at a higher temperature (approximately 50° C.) and at a less weak pressure (~25×10$^3$ Pa, or 250 mbar), which, however, remains very much less than the boiling temperature of the solvent in the solution. Operating conditions of these kinds are advantageous from the standpoint of performing the process, since it is easy to operate at ambient temperature or with heating, and with a low pressure for withdrawal of the solvent, leading to rapid evaporation of said solvent, thereby allowing a reduction to be achieved in the time taken to perform the process. However, the application of a low pressure, very much lower than the boiling pressure of the solvent in the solution, from the beginning of the evaporation process gives rise to intense boiling of said solvent (a foaming effect then develops), which is difficult to reconcile with reproducible control over the process, especially at the start of withdrawal of said solvent.

The crude CL20 crystals obtained take the bipyramidal form and are usually twinned. These crystals have an elongation ratio (see the definition of this parameter hereinafter) of more than 2, or even more than 4, for more than 90% (by number), or even for the entirety, of the crystals.

Crystals of these kinds are of the same type as those shown in attached FIG. 2A (twinned crystals obtained with the ethyl acetate/HFE 7500 solvent/nonsolvent pairing) and FIG. 2B (crystals obtained with the acetone/toluene solvent/nonsolvent pairing, and shown at higher magnification) (photographs taken with an optical microscope in transmission). These figures should be considered with the examples below.

This kind of morphology of its crystals makes CL20 poorly suited to formulation when high charge levels are the aim. The reason is that the production of compositions of high charge level is compromised because of the large increase in viscosity that is inevitably associated with high charge levels. Moreover, the presence of sharp ridges on the crystals makes them more sensitive to standard pyrotechnic safety trials.

The skilled person therefore wishes to have CL20 crystals of rounded form (rounded=compact, nonacicular, for example, cubic or near-spherical) which are obtained by a simple, controlled process.

For this purpose, patent application CN-A-101624439 proposes the production of CL20 by a process of the same type as that already described by the present applicant in patent application FR-A-2 884 244 for producing ammonium dinitroamide crystals. That process involves introducing, into a solution containing CL20, an effective and nonexcessive amount of at least one crystal habit modifier, said at least one crystal habit modifier, during the generation of the crystals, steering the growth of the crystal faces and leading to rounded CL20 crystals. Firstly, this process cannot be transposed to the industrial scale without a necessary prior step of industrial qualification, and secondly it requires the addition of one or more habit modifiers, traces of which inevitably remain to contaminate the end product.

In this kind of context, in reference to the technical problem of formulating CL20 crystals (formulation at high charge levels), the present applicant proposes an entirely original solution which overcomes the prejudices of the skilled person documenting the impossibility of obtaining, by simple crystallization, rounded CL20 crystals better suited to the formulation of energetic materials. This solution is based neither on conditioning of the crude crystals (by mechanical erosion, for example) nor on the intervention of a crystal habit modifier during the generation of the crystals, but on control of the crystalline growth parameters (the parameters of the crystallization process), which allow rounded crystals to be obtained which have a selected particle size range, ranging from a few microns to a number of hundreds of microns.

Modifying the crystalline growth parameters (the parameters of the crystallization process) in order to generate crystals in an original crystalline form is not an innovative operation in itself. The parameters in question, such as the nature of the solvent, especially its viscosity, for steering the relative rates of transfer and of integration of the atoms in the crystal, the temperature cycles for shifting the equilibrium of the solution on the solubility diagram, the presence of impurities, and agitation, are known to the skilled person. The modification of said parameters, however, has never been described, and even less so controlled, to the knowledge of the present applicant, in the context of obtaining CL20 crystals, in reference to the technical problem of formulating pyrotechnic articles.

In this particular context, the inventors have shown, quite surprisingly, that it is possible to perform the process of crystallizing CL20 in solution in a solvent/nonsolvent mixture (a process of the type described in patent applications EP-A-0 913 374 and FR-A-2 950 623) for the purpose of obtaining rounded crystals, while retaining the conventional procedure, but by imposing parameters of evaporation of the solvent (low temperature and adjusted and controlled pressure).

According to a first subject, therefore, the present invention relates to a process for obtaining CL20 crystals. The process in question is of the type described in patent application EP-A-0 913 374. Said process in fact involves an improvement to said process according to patent application EP-A-0 913 374. This improvement is of particular interest in reference to the industrial-scale exploitation of said process according to patent application EP-A-0 913 374.

The process of the invention is more specifically a process for obtaining a charge of hexanitrohexaazaisowurtzitane crystals, which process comprises:
preparing a saturated solution of any polymorphic form of hexanitrohexaazaisowurtzitane in a mixture comprising both an organic solvent for said hexanitrohexaazaisowurtzitane and an organic nonsolvent for said hexanitrohexaazaisowurtzitane, said solvent being more volatile than said nonsolvent (said solvent and nonsolvent being obviously miscible in the proportions in which they are employed for the constitution of the mixture containing the CL20 (i.e., for the constitution of said saturated solution));
seeding this saturated solution with a few hexanitrohexaazaisowurtzitane crystals; and then
concentrating the seeded, saturated solution by at least partial evaporation of the solvent.

Thus far, the process of the invention is a process of the type described in patent applications EP-A-0 913 374 and FR-A-2 950 623.

Characteristically, in accordance with the invention, the evaporation of the solvent (for the concentration of the seeded, saturated solution) is performed at a temperature of between 35° C. and 15° C. and at a pressure adjusted, to plus or minus $1.2 \times 10^3$ Pa (+/−12 mbar), to the boiling pressure of the solvent in said solution, throughout the process of evaporating said solvent from said solution.

Said organic solvent for the CL20 is advantageously selected from the group consisting of esters, nitriles, ethers, ketones, and mixtures thereof, and/or, advantageously and, said organic nonsolvent for the CL20 is advantageously selected from the group consisting of aliphatic hydrocarbons (such as alkanes and especially hexane, heptane, and octane), halogenated aliphatic hydrocarbons (such as chlorinated aliphatic hydrocarbons and especially 1,2-dichloroethane), aromatic hydrocarbons (such as toluene and xylenes), nonflammable hydrofluoroethers (such as 2-trifluoromethyl-3-ethoxydodecafluorohexane), and mixtures thereof. Acetone (solvent) is presently not excluded in so far as the process of the invention, owing to its optimization of the parameters of temperature and pressure, makes it possible to use acetone (particularly in the context of the use of an acetone/toluene solvent/nonsolvent pairing) to obtain interesting charges of crystals.

It is understood that the pressure applied, close, to plus or minus $1.2 \times 10^3$ Pa (+/−12 mbar), to the boiling pressure of the solvent in the solution, decreases as the solvent is withdrawn by evaporation (the concentration of solvent in the solution reduces as it is withdrawn, and, consequently, its boiling pressure at constant temperature reduces).

The (evaporation) pressure applied during the withdrawal of the solvent from the solution (the withdrawal to the CL20-charged solvent/nonsolvent mixture) is advantageously equal, to plus or minus $5 \times 10^2$ Pa (5 mbar), to the boiling pressure of said solvent, very advantageously equal to plus or minus 1 mbar to the boiling pressure of said solvent.

The process of the invention is therefore performed at a constant, not very high temperature, and at a nonconstant, developing pressure, which coincides, to about plus or minus $1.2 \times 10^3$ Pa (+/12 mbar), to the boiling pressure of the solvent in the solvent/nonsolvent mixture (the pressure of the solvent developing owing to the progressive evaporation of said solvent). It is understood that for each solvent/nonsolvent pairing, a prior calibration must be performed.

Advantageously, at the startup of evaporation (of withdrawal) of the solvent, the pressure applied to the solution (solvent/nonsolvent mixture) is greater than the boiling pressure of the solvent within the limits indicated above. Since the proportion of solvent in the solution is high at said startup of evaporation, intensive boiling of said solvent is so avoided (and hence agitation of the solution by "turbulent" boiling is avoided), this being particularly marked at low temperature and having the capacity to induce uncontrolled effects on the crystallization process.

The evaporation temperature is between 35° C. and 15° C.

Monitoring of the parameters of temperature (fixed parameter) and pressure (developing) of evaporation of the solvent has been found to be absolutely vital for resulting in the production of rounded CL20 crystals.

The amounts of solvent and crystals (in suspension) in the suspension obtained at the end of the concentration procedure are of course dependent on the precise way in which this concentration procedure is performed (on the degree of evaporation of the solvent employed). The degree of evaporation of the solvent may be greater or lesser. The crystals may therefore be obtained in suspension in a solvent/nonsolvent mixture whose liquid phase contains, in particular, less than 15% by mass of solvent, advantageously less than 5% by mass of said solvent. If the aim is to obtain suspensions (of crystals in the nonsolvent) that are virtually free from solvent, the process of the invention comprises evaporating said solvent from the seeded solution (advantageously extensive evaporation) and also the washing, with the nonsolvent, of the resulting suspension.

The resulting suspension, whose liquid phase comprises the nonsolvent or a solvent/nonsolvent mixture (with a greater or lesser proportion of solvent), may, according to a first variant, be stored as it is and used in a process for manufacturing an energetic material, including the (total or virtually total) extraction of said liquid phase (see later on below). According to another variant, said suspension may be filtered to recover the crystals (the charge of crystals or solid phase) that it contains, said crystals being subsequently used in a process for manufacturing energetic material. One or other of these variants is appropriately employed in view of the exact nature of the liquid phase (in particular, the nature of the nonsolvent) of the suspension.

The saturated solution is advantageously seeded with hexanitrohexaazaisowurtzitane crystals of epsilon ($\epsilon$) polymorphic form, to give a suspension of hexanitrohexaazaisowurtzitane crystals of epsilon ($\epsilon$) polymorphic form in a liquid phase. According to this embodiment, said saturated solution is preferably saturated with CL20 of a polymorphic form other than the epsilon ($\epsilon$) form.

The preferred solvent/nonsolvent pairings are as follows: ethyl acetate/HFE 7500, ethyl acetate/toluene, and acetone/toluene. The ethyl acetate/HFE 7500 pairing is particularly preferred.

The ratio by mass of the solvent/nonsolvent pairing is typically between 10/90 and 50/50, advantageously between 15/85 and 35/65. It is generally adjusted for a saturation solubility of CL20 of 100 g/L to 200 g/L, in order on the one hand to limit the pyrotechnic risks and on the other hand to prevent possible abrasion of the crystals by mutual rubbing in the solution.

The process of the invention, owing to the control of the conditions under which the solvent is evaporated, leads to crystals (and not agglomerates or crystal twins) being obtained that are of very particularly interesting rounded form, different from those of the prior art in the bipyramidal form which are usually twinned. It does not lead to the production of only a few crystals of this type. The process of the invention leads more precisely to a charge of crystals of this type being obtained. Said charge thus advantageously includes at least 80% (by number), very advantageously more than 80% (by number), or even more than 90% (by number) of crystals (untwinned crystals) having an elongation ratio of less than or equal to 1.5. Said elongation ratio is very generally between 1.5 and 1. It is noted, moreover, that the charge of the crystals of the invention is not contaminated (that the crystals which constitute said charge are not contaminated) by the involvement of any crystal habit modifier (during the growth of said crystals).

The "elongation ratio" parameter, used in reference to the crystals of the invention, is conventionally defined as the ratio, for a crystal, of its maximum Feret diameter to its minimum Feret diameter, said maximum Feret diameter corresponding to the maximum distance between two parallel tangents on opposite sides of the crystal, and said minimum Feret diameter corresponding to the minimum distance between two parallel tangents on opposite sides of the crystal.

It is also noteworthy that said crystals, relative to those of the prior art, exhibit a reduced sensitivity, as shown in the examples below.

According to a second subject, therefore, the present invention relates to a charge of crystals obtainable by the process described above (first subject of the invention), and more particularly a charge exhibiting the features set out above. In light of the proposals above, it is understood that a charge of crystals of this kind may take the form of a suspension (crystals in suspension in a liquid phase) or exist in the "dry state" (crystals recovered after filtration).

According to its third subject, the present invention relates to an energetic material comprising at least one such charge, in the dry state (charge per se or as obtained by said process). Said energetic material therefore comprises hexanitrohexaazaisowurtzitane crystals, and at least some of said crystals are crystals from a charge of the invention. Said crystals may be present in dispersion in an energetic or nonenergetic binder. The presence of the binder, however, is in no way mandatory. The energetic material comprises at least one charge of crystals in the dry state (charge of the invention) but may have been prepared from a charge of crystals of this kind in the dry state or from a suspension of crystals (see below). Its manufacture according to this second variant constitutes the fourth and final subject of the invention.

According to its fourth subject, therefore, the present invention relates to the manufacture of an energetic material comprising hexanitrohexaazaisowurtzitane crystals. The process for manufacturing said material, in accordance with the invention, comprises, conventionally, the introduction and mixing of the ingredients (binder, crosslinking agent, charge(s), etc.) in a mixer (to form a paste). Characteristically, the process comprises introducing CL20 crystals not in the form of crystals but within a suspension obtained according to the invention (charge of crystals according to the invention in the form of a suspension (the liquid phase of said suspension is a solvent/nonsolvent mixture which advantageously is rich in nonsolvent or is even almost exclusively composed of the nonsolvent)). Said suspension is used as a source of said crystals, as an ingredient or raw material. Within the suspension, the crystals are phlegmatized. The liquid phase of said suspension is subsequently removed by extraction, extraction under vacuum, complete or virtually complete. This manufacturing process, which therefore uses a suspension of crystals as a source of said crystals, may be performed at the end of the production of said suspension or at a later time than said production (after storage of the resulting suspension, or after transport thereof, or after storage and transport thereof, or else after transport and storage thereof). It is understood that the energetic material may thus be obtained with a great flexibility. The phlegmatization of the crystals within the suspension, which is the basis for this flexibility in implementation of the process, is particularly advantageous.

It should be noted that it is entirely possible, in the context of the performance of another process for manufacturing an energetic material, to use dry crystals obtained from the process of the present invention (at least one charge of crystals in the dry state), or dried crystals of the present invention (at least one charge of crystals in the dry state) which have been suspended in another nonsolvent (water, for example).

The invention is now illustrated, in a way which is not limitative at all, by the appended figures and examples below.

The HFE 7500 used (2-trifluoromethyl-3-ethoxydodecafluorohexane) is sold by 3M.

EXAMPLE A AND COMPARATIVE EXAMPLE B

The process of the invention is performed, in accordance with example A from Table 3 (see below), in a reactor having a volume of 60 L. The evaporative crystallization is performed from an ethyl acetate (solvent)/HFE 7500 (nonsolvent) solution saturated with CL20, said solvent, nonsolvent, and CL20 being present, respectively, in the following proportions by mass: 30.1%/61.8%/8.1%.

As a customary component, on the distillation assembly, there is a stirrer which has a thin profile, which does not cause significant breaking but has a good pumping capacity, making it possible to overcome the separation of the crystals by settling under rotary conditions while avoiding breakage at the blade end. During operation, this allows the crystals to be passed continually in growth phase to the evaporation interface (where the solution becomes desaturated) without subjecting them to excessive stress "mechanically".

After the CL20-saturated starting solution has been introduced into the reactor, the temperature of said solution is raised to 20° C. and then the seed is introduced (110 g of CL20ε with an average size of 30 μm). Under these conditions, the boiling pressure of the solvent in the solution (solvent/nonsolvent) is $17 \times 10^3$ Pa (170 mbar). The process of evaporation begins by subjecting the solution to a withdrawal pressure of $18 \times 10^3$ Pa (180 mbar), slightly higher (+10 mbar) than the boiling pressure of the solvent, in order to prevent mass boiling of the solvent, which is liable to interfere (by stirring of the solution) with the phenomenon of crystallization of the CL20. Ethyl acetate is then withdrawn gradually for 5 and a half hours by adjustment of the pressure applied to the solution, within the limits of +/-$1 \times 10^3$ Pa (+/-10 mbar) around the boiling pressure of said solvent. The pressure applied therefore follows a value which is set within the template imposed. The pressure at the end of withdrawal is 80 mbar. The proportion by mass of solvent at the end of withdrawal is approximately 10%. The pressure is then returned to atmospheric pressure and the suspension of CL20ε in the solvent/nonsolvent mixture is discharged.

For electron microscopy analysis of the CL20ε crystals from the suspension, the suspension is filtered and the retentate is pulled dry. The product is subsequently dried in an oven.

Figure 1A:
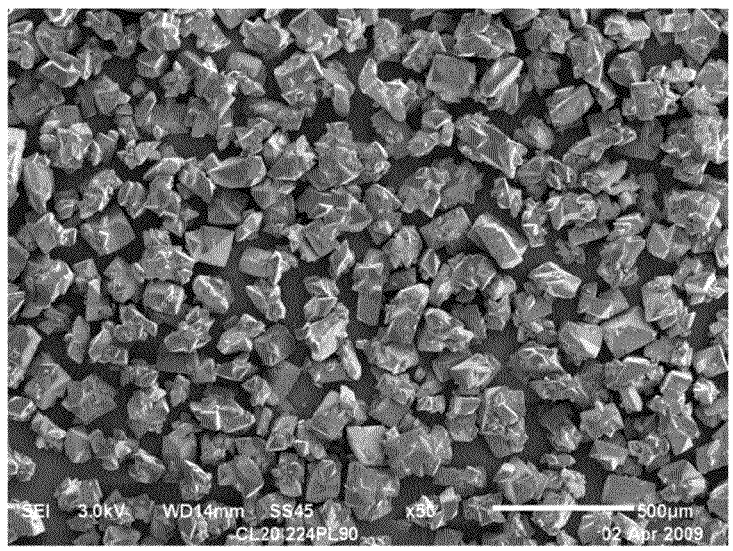
FIGS. 1A and 1B show rounded crystals, obtained by the process of the invention implemented, respectively, with an ethyl acetate/HFE (1A) and with an acetone/toluene (1B) solvent/nonsolvent solution (see the examples below).

Recovered on the filter is a crystalline product, off-white in color, composed of rounded CL20ε crystals with a median diameter of 122 μm, which are not twinned, having an elongation ratio of less than 1.5 for more than 90% of them (% by number), as are shown in FIG. 1A.

Figure 2A:
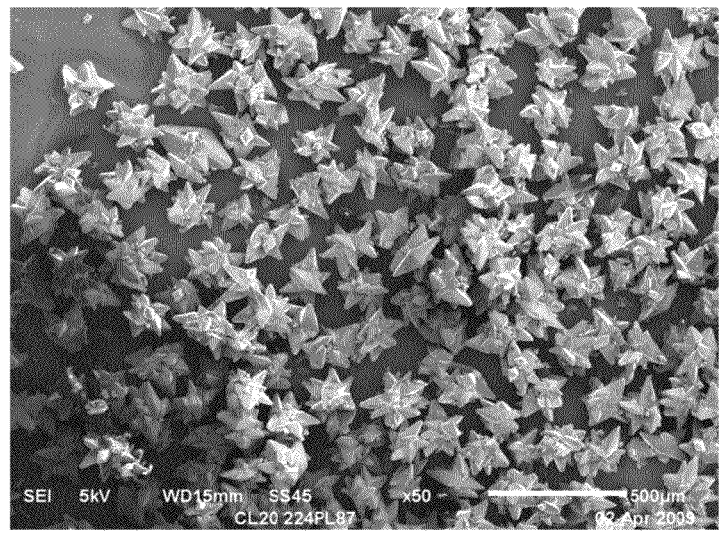
FIGS. 2A and 2B show twinned bipyramidal crystals, obtained, respectively, with an ethyl acetate/HFE 7500 (2A) and with an acetone/toluene (2B) solvent/nonsolvent solution, under (temperature) conditions which are not those of the invention (see the comparative examples below).

Example B from Table 3 relates to the preparation of crystals under hot conditions while controlling the pressure parameter in accordance with the invention. For a saturated solution close to that of example A (see said Table 1), the solvent is gradually distilled for 2 hours 10 minutes, during which the distillation temperature is raised to 67° C. and the pressure applied to the solution is adjusted to slightly below the boiling point of the solvent, the pressure then ranging between $42.5 \times 10^3$ Pa (425 mbar) and $32.5 \times 10^3$ Pa (325 mbar). At the end of distillation, the proportion by mass of solvent at the end of withdrawal is approximately 5%. Recovered on the filter is a crystalline product, off-white in color, composed of CL20ε crystals in the bipyramidal form, with an elongation ratio of more than 2 for more than 90% of them (% by number), most of these crystals being twinned, with a median diameter of 115 μm, as are shown in FIG. 2A.

This comparative example B demonstrates that adjusting the pressure parameter (according to the invention) is not enough to produce the crystals of the invention. It is necessary, in accordance with the invention, to combine a relatively low temperature and adjustment of the pressure in order to obtain the desired crystalline morphology.

The crystals obtained by the process of the invention therefore exhibit a rounded shape which is favorable to the production of energetic materials incorporating them with high charge levels.

Furthermore, they exhibit reduced sensitivity in tests of pyrotechnic sensitivity, as for example in the impact sensitivity test (ISI)*, and to the sensitivity test of the "detonation priming through a barrier" type, also called DPI* (Detonation Proclivity Index): see the results indicated in Table 1 below. Details of said tests are given later on below.

*ISI: The trial conducted corresponds to that described in the NFT 70-500 standard, which is itself similar to the UNO 3a)ii) trial resulting from the "Recommendations relating to the Transport of Dangerous Goods—Manual of tests and criteria, fourth, revised edition, ST/SG/AC.10/11/Rev.4, ISBN 92-1-239083-8ISSN 1014-7179". By a minimum series of 30 tests, a determination is made of the energy producing 50% of positive results (Bruceton method for processing the results) of an explosive material subjected to the impacts for hammer. The material under test is confined in a steel device composed of two discs and a guide ring. By modifying the mass and the drop height of the hammer, the energy may be varied from 1 to 50 J.

**DPI: The trial is carried out in accordance with the standard NF T 70-502 (see also UNO—Recommendations relating to the Transport of Dangerous Goods—Manual of tests and criteria, fourth, revised edition, ST/SG/AC.10/11/Rev.4, ISBN 92-1-239083-8ISSN 1014-7179 and STANAG 4488). It involves determining the reactivity of an explosive substance subjected to detonation from a priming relay through a barrier composed of cellulose acetate cards. A determination is made of the limiting thickness of the barrier for which the detonation of a second relay, placed in contact with the other face of the test specimen, is not primed.

TABLE 1

| | Properties of the crystals obtained | | |
|---|---|---|---|
| | Dmedian (μm) | ISI (J) | DPI (cards) |
| A (invention) | 122 | 4 | 335 |
| B (comparative example) | 115 | 2.7 | >360 |

EXAMPLE C AND COMPARATIVE EXAMPLE D

The process of the invention is performed, in accordance with example C from Table 4 (see below), in a reactor having a volume of 60 L. The evaporative crystallization is performed from an acetone (solvent)/toluene (nonsolvent) solution saturated with CL20, said solvent, nonsolvent, and CL20 being present, respectively, in the following proportions by mass: 18.1%/72.6%/9.3%.

The solvent is distilled gradually over 5 hours, with the distillation temperature raised to 20° C. and the pressure applied to the solution adjusted to between $10 \times 10^3$ Pa (100 mbar) and $3.5 \times 10^3$ Pa (35 mbar), in accordance with the same procedure as for example A.

Figure 1B:
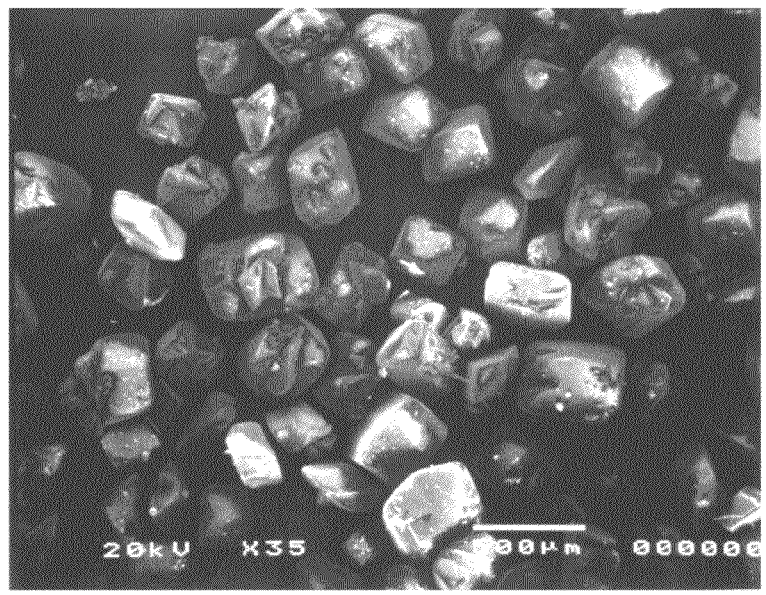

Recovered on the filter is a crystalline product, off-white in color, composed of rounded CL20ε crystals with a median diameter of 236 μm, which are not twinned, having an elongation ratio of less than 1.5 for more than 90% of them (% by number), as are shown in FIG. 1B.

Figure 2B:
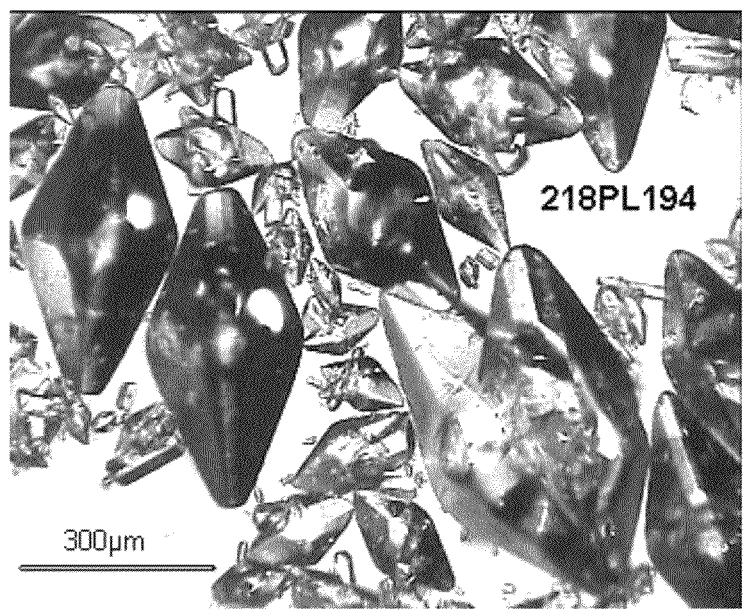

Example D from Table 4 relates to the preparation of crystals under hot conditions while controlling the pressure parameter in accordance with the invention. For a solution close to that of example C (see said Table 4), the solvent is gradually distilled for 3 hours 20 minutes, during which the distillation temperature is raised to 67° C. and the pressure applied to the solution is adjusted to slightly below the boiling point of the solvent, the pressure then ranging between $69.5 \times 10^3$ Pa (695 mbar) and $35 \times 10^3$ Pa (350 mbar). Recovered on the filter is a crystalline product, off-white in color, composed of CL20ε crystals in a bipyramidal form, with an elongation ratio of more than 2 for more than 90% of them (% by number), most of these crystals being twinned, with a median diameter of 213 μm. FIG. 2B shows crystals, more particularly examples of untwinned crystals, obtained by the process of example D. As for example B, example D shows that the adjustment solely of the pressure parameter (according to the invention) does not produce the desired crystal morphology.

The crystals obtained by the process of the invention therefore exhibit a rounded shape which is favorable to the production of energetic materials incorporating them with high charge levels.

Furthermore, they exhibit reduced sensitivity in tests of pyrotechnic sensitivity, as for example in the deflagration-detonation transition (DDT)*** test, and in the test of measurement of combustion rate at atmospheric pressure (linear combustion trial of the product in powder form in a chute): see the results indicated in Table 2 below. Details of said DDT test are given later on below.

***DDT. The test involves measuring the proclivity of a mass of divided material (particle bed) to pass from combustion to detonation following ignition, carried out on the surface of the bed, specifically for CL20, otherwise at the base of the powder bed. SNPE test 55 involves filling a metal tube of 40 mm (test 55A) or 10 mm (test 55B) diameter and of variable height. The tube is open at one end. The critical height resulting in a violent reaction is determined from the effects observed on the tube.

TABLE 2

| | Properties of the crystals obtained | | |
|---|---|---|---|
| | Dmedian (μm) | DDT (phi 10 mm) | Rc chute (mm/s) |
| C (invention) | 236 | 150 mm combustion 175 mm explosion | 127 |
| D (comparative example) | 213 | 75 mm combustion 100 mm explosion | 210 |

TABLE 3

| Example | Volume of the solution | % by mass (solution) | | | CL20 ε crystal seed | | Solvent evaporation conditions | | | Properties of the crystals obtained | | | |
|---|---|---|---|---|---|---|---|---|---|---|---|---|---|
| | | CL20 | HFE7500 | Ethyl acetate | Dmedian (μm) | Mass (kg) | T (°C.) | Vacuum range ($10^3$ Pa) | Time | Dmedian (μm) | ISI (J) | DPI (cards) | Morphology of crystals |
| A | 60 L | 8.1 | 61.8 | 30.1 | 30 | 0.11 | 20 | 20 to 8 | 5 h 30 min | 122 | 4 | 335 | Rounded |
| B | 60 L | 7.5 | 57.1 | 35.4 | 6 | 0.11 | 67 | 42.5 to 34.5 | 2 h 10 min | 115 | 2.7 | >360 | Bipyramidal, twinned |

TABLE 4

| Example | Volume of the solution | % by mass (solution) | | | CL20 ε crystal seed | | Solvent evaporation conditions | | | Properties of the crystals obtained | | | |
|---|---|---|---|---|---|---|---|---|---|---|---|---|---|
| | | CL20 | Toluene | Acetone | Dmedian (μm) | Mass (kg) | T (°C.) | Vacuum range ($10^3$ Pa) | Time | Dmedian (μm) | DDT phi 10 | Rc chute mm/s | Morphology of crystals |
| C | 60 L | 9.3 | 72.6 | 18.1 | 150 | 0.1 | 20 | 10 to 3.5 | 5 h 0 min | 236 | 150 mm comb 175 mm expl | 127 | Rounded |
| D | 60 L | 9.4 | 72.5 | 18.1 | 150 | 0.12 | 67 | 69.5 to 35 | 3 h 20 min | 213 | 75 mm comb 100 mm expl | 210 | Bipyramidal, twinned |

The invention claimed is:

1. A process for obtaining a charge of hexanitrohexaazaisowurtzitane crystals, said process comprising:
   preparing a saturated solution of any polymorphic form of hexanitrohexaazaisowurtzitane in a mixture comprising both an organic solvent for said hexanitrohexaazaisowurtzitane and an organic nonsolvent for said hexanitrohexaazaisowurtzitane, said organic solvent being more volatile than said organic nonsolvent;
   seeding the saturated solution with a few hexanitrohexaazaisowurtzitane crystals to form a seeded saturated solution; and then
   concentrating the seeded saturated solution by at least partial evaporation of the organic solvent, said evaporation of the organic solvent being performed at a temperature of from 35° C. to 15° C. and at a pressure that is in a range from a boiling pressure of the organic solvent in the seeded saturated solution plus $1.2 \times 10^3$ Pa (12 mbar) to the boiling pressure of the organic solvent in the seeded saturated solution minus $1.2 \times 10^3$ Pa (12 mbar) throughout the process of evaporating said organic solvent from said seeded saturated solution.

2. The process according to claim 1,
   wherein said organic solvent is selected from the group consisting of esters, nitriles, ethers, ketones, and mixtures thereof; or
   said organic nonsolvent is selected from the group consisting of aliphatic hydrocarbons, halogenated aliphatic hydrocarbons, aromatic hydrocarbons, nonflammable hydrofluoroethers, and mixtures thereof.

3. The process according to claim 1, wherein said evaporation of the organic solvent is performed at the pressure that is in a range from a boiling pressure of the organic solvent in the seeded saturated solution plus $5 \times 10^2$ Pa (5 mbar) to the boiling pressure of the organic solvent in the seeded saturated solution minus $5 \times 10^2$ Pa (5 mbar) throughout the process of evaporating said organic solvent from said seeded saturated solution.

4. The process according to claim 1, wherein the pressure on startup of the evaporation is greater than the boiling pressure of the solvent in said solution.

5. The process according to claim 1, wherein said organic solvent is evaporated to give a suspension of the crystals in a solvent/nonsolvent mixture, said solvent/nonsolvent mixture containing less than 15% by mass of the organic solvent.

6. The process according to claim 5, which further comprises washing said suspension with the organic nonsolvent.

7. The process according to claim 1, which further comprises recovering the crystals by filtration.

8. The process according to claim 1, wherein seeding is carried out with crystals of polymorphic form $\epsilon$.

9. A charge of crystals which is obtainable by the process according to claim 1.

10. The charge of crystals according to claim 9, wherein at least 80% of the crystals in the charge have an elongation ratio of less than or equal to 1.5.

11. The process according to claim 1, wherein said organic solvent is selected from the group consisting of esters, nitriles, ethers, ketones, and mixtures thereof, and said organic non solvent is selected from the group consisting of aliphatic hydrocarbons, halogenated aliphatic hydrocarbons, aromatic hydrocarbons, nonflammable hydrofluoroethers, and mixtures thereof.

12. The process according to claim 1, wherein said organic solvent is evaporated to give a suspension of the crystals in a solvent/nonsolvent mixture, said solvent/nonsolvent mixture containing less than 5% by mass of the organic solvent.

13. The process according to claim 12, wherein it further comprises washing said suspension with the organic nonsolvent.

14. The process according to claim 1, wherein said seeding is carried out with crystals of polymorphic form $\epsilon$, the saturated solution containing hexanitrohexaazaisowurtzitane in a polymorphic form other than the $\epsilon$ polymorphic form.

15. The charge of crystals according to claim 9, wherein at least 80% of the crystals in the charge have an elongation ratio between 1.5 and 1.

* * * * *